US00PP07919P

United States Patent [19]

Veenstra

[11] Patent Number: Plant 7,919

[45] Date of Patent: Jul. 21, 1992

[54] ASIATIC LILY NAMED MOON PIXIE

[75] Inventor: Rien Veenstra, Wilsonville, Oreg.

[73] Assignee: Oregon Bulb Farms, Inc., Aurora, Oreg.

[21] Appl. No.: 504,285

[22] Filed: Mar. 19, 1990

[51] Int. Cl.[5] ..... A01H 5/00

[52] U.S. Cl. ..... Plt./87.4

[58] Field of Search ..... Plt./68

*Primary Examiner*—James R. Feyrer

[57] ABSTRACT

A new variety of Asiatic lily hybrid of the chalice type particularly distinguished by its particular mimosa yellow and canary yellow coloration of a flower of medium size produced profusely on a relatively short stem and having abundant foliage for pot plant culture. This plant flowers annually in mid-season and has a vigorous and upright growth habit with a capability of being forced for year round crop production.

1 Drawing Sheet

BACKGROUND OF THE NEW PLANT

This new lily variety originated as a seedling resulting from the crossing of two plants of the same variety with the object of producing pot plants having different and attractive color characteristics. The present seedling was selected by me for propagation because of its attractive and interesting flower coloration in combination with its vigorous and strong growth and abundant foliage and asexual reporduction of this seedling was carried on under my direction through several successive generations by scales and by tissue culture procedures at Sandy, Oreg. with very satisfactory results which demonstrated conclusively that the novel and desirable characteristics of the selected seedling would hold true from generation to generation and appear to be firmly fixed.

DESCRIPTION OF THE DRAWING

My new variety of lily plant is illustrated by the accompanying photographic drawing which, in full color, shows a three-quarter face view of a fully opened and mature blossom, the color rendition being as nearly true as can be reasonably obtained by conventional photographic procedures.

DESCRIPTION OF THE NEW PLANT

The following is a detailed description of my new variety of asiatic lily as observed at Oregon Bulb Farms, Inc. in Aurora, Oreg. the color designations being according to The R.H.S. Colour Chart published by The Royal Horticultural Society of London, England.

THE PLANT

Origin: Seedling.

Parentage:

*Seed parent.*—An unnamed clone of a hybrid resulting from the crossing of the variety Moon Glow by the variety Red Carpet, both unpatented.

*Pollen parent.*—A clone of the same variety as the seed parent.

Classification: Asiatic hybrid of the chalice type.

Form: An erect single stem.

Height: About 40 to 45 cm.

Main stem length: 40 to 45 cm.

Growth habit: Vigorous, upright and strong.

Foliage:

*Quantity.*—Abundant.

*Size of leaf.*—About 6 to 9 cm. long and about 1.75 to 2.5 cm. wide.

*Shape of leaf.*—Lanceolate with entire margins.

*Texture.*—Leathery.

*Aspect.*—Glossy.

*Color.*—Upper side — Yellow-Green 147-A. Under side — Yellow-Green 146-A.

Bulbs: Range in size up to about 25 cm. in circumference for commercial use.

*Color.*—White.

The Bud

Size: Medium.

Length: About 9 cm.

Diameter: About 3 cm.

Shape: Long ovoid with obtuse apex.

Rate of opening: The bud opens slowly at maturity in response to light.

Color of tepals:

*When sepals first divide.*—Yellow 7-A.

*When tepals begin to unfurl.*—Yellow 7-A.

Peduncle:

*Character.*—Strong and erect.

*Color.*—Yellow-Green 144-A mottled with greyed purple 183-A.

THE FLOWER

Blooming habit: Annually and profusely at mid-season.

Size of flower: Very large.

*Diameter.*—About 14 cm.

*Depth.*—About 8 cm.

Borne: In a cluster having a raceme arrangement.

Shape:

*When bloom first opens.*—Cup shaped.

*When bloom matures.*—Somewhat flatened cup shape.

Tepalage:

*Number.*—Six.

*Arrangement.*—Hexagonal and imbricated.

Form: Elliptical with entire margins and acute apex.

Texture: Leathery.

Aspect: Satiny.

Color:

*Outer tepals.*—Body Mimosa Yellow 8-B to Aureolin 12-A with base of Mimosa Yellow 8-D.

*Inside tepals.*—Body Yellow 8-B to 9-B with base of Yellow 8-D.

Pedicel:

*Length.*—About 5.5 cm.

*Color.*—Yellow-Green 144-A mottled with greyed purple 183-A.

*Character.*—Strong and upright, ascending upwardly to about 55° from the horizontal.

Discoloration after full bloom: Very little color change with age.

Persistance: About three weeks.

Fragrance: None.

Disease resistance: Resistant to fusarium and tolerant of virus as observed at Aurora, Oreg.

THE REPRODUCTIVE ORGANS

Stamens:

*Number.*—6.

*Arrangement.*—Typical of genus Lilium.

*Anthers.*—Size: About 2 cm. Color: Greyed purple 186-A.

*Filaments.*—Length: About 6.5 cm. Color: Yellow 10-D.

*Pollen.*—Color: Orange 28-B.

Pistils:

*Number.*—1.

*Styles.*—Length: About 5.5 cm. Color: Green-Yellow 1-B.

*Stigma.*—Color: Greyed Red 182-A.

Character of ovaries: Typical of the genus Lilium.

FRUIT

Fertility: The fruit is fertile.

Shape: Ovoid.

Color at maturity: Soft brown.

Compared with lily Butter Pixie (U.S. Plant Pat. No. 6,422) my new variety is of a lighter yellow color and is unspotted. The flower remains more cup shaped and the tepals are wider. The foliage is more dense and each leaf of the new variety is broader. The keeping quality of the bulb is excellent and no scorch or bud abortion problems have been observed. The plant is a very consistent forcer throughout the year.

I claim:

1. The new and distinctive Asiatic lily substantially as herein described, particularly distinguished by the yellow coloration of its relatively large blooms which are produced profusely on strong upright stems at a height of about 40–45 cm.

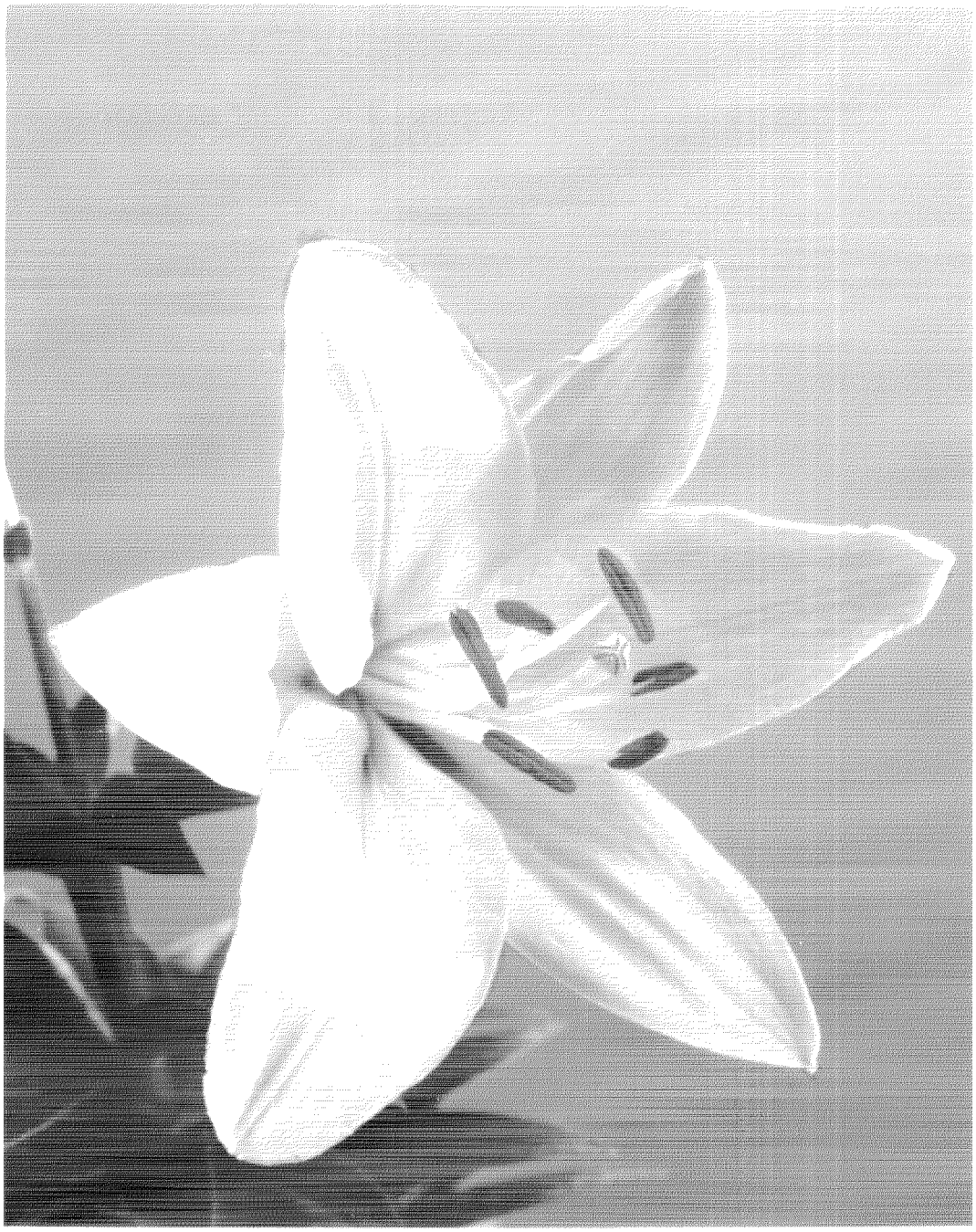

* * * * *